US011419956B1

(12) United States Patent
Mayfield, III

(10) Patent No.: US 11,419,956 B1
(45) Date of Patent: Aug. 23, 2022

(54) LIGHT FIXTURE WITH REMOVABLE AUXILIARY LIGHT MODULES

(71) Applicant: ABL IP Holding LLC, Atlanta, GA (US)

(72) Inventor: John T. Mayfield, III, Covington, GA (US)

(73) Assignee: ABL IP Holding LLC, Atlanta, GA (US)

( * ) Notice: Subject to any disclaimer, the term of this patent is extended or adjusted under 35 U.S.C. 154(b) by 0 days.

(21) Appl. No.: 17/218,577

(22) Filed: Mar. 31, 2021

(51) Int. Cl.
| | |
|---|---|
| *A61L 2/10* | (2006.01) |
| *F21V 23/00* | (2015.01) |
| *F21V 23/04* | (2006.01) |
| *A61L 2/26* | (2006.01) |
| *F21Y 115/10* | (2016.01) |

(52) U.S. Cl.
CPC .......... *A61L 2/10* (2013.01); *A61L 2/26* (2013.01); *F21V 23/003* (2013.01); *F21V 23/0471* (2013.01); *A61L 2202/11* (2013.01); *A61L 2202/14* (2013.01); *F21Y 2115/10* (2016.08)

(58) Field of Classification Search
CPC .......... A61L 2/10; A61L 2/26; A61L 2202/11; A61L 2202/14; A61L 9/20; A61L 2209/12; A61L 2209/00; F21V 23/003; F21V 23/0471; F21V 23/007; F21Y 2115/10; F24F 13/06; F24F 2221/02
See application file for complete search history.

(56) References Cited

U.S. PATENT DOCUMENTS

| | | | |
|---|---|---|---|
| 10,166,309 B2 * | 1/2019 | Liao | C02F 1/008 |
| 2010/0196214 A1 * | 8/2010 | Graff | F24F 8/10 |
| | | | 422/120 |
| 2017/0321877 A1 * | 11/2017 | Polidoro | A61L 9/20 |

OTHER PUBLICATIONS

Light Engine Module Assembly Shown with Two UV Modules (available at least as early as Feb. 19, 2021), 1 page.
U.S. Appl. No. 17/313,193, Titled: Techniques for Directing Ultraviolet Energy Towards a Moving Surface, filed May 6, 2021, 74 pages.
U.S. Appl. No. 17/313,204, Titled: Techniques for Directing Ultraviolet Energy Towards a Moving Surface, filed May 6, 2021, 76 pages.

* cited by examiner

*Primary Examiner* — Bao Q Truong
(74) *Attorney, Agent, or Firm* — Kilpatrick Townsend & Stockton LLP

(57) ABSTRACT

A light fixture includes a housing defining a channel and an insert lighting module. The insert lighting module includes an insert housing, a visible light engine coupled to a bottom portion of the insert housing for emitting visible light for general illumination, and an auxiliary light module coupled to the insert housing and including an auxiliary light engine for emitting germicidal light effective in deactivating pathogens. A top portion of the insert lighting module may be positioned within the channel and the insert lighting module may be coupled to the housing. The auxiliary light module may be uncoupled and removed from the insert housing by performing the steps of: uncoupling the insert lighting module from the housing and removing the insert lighting module from the channel, and uncoupling the auxiliary light module from the insert housing and removing the auxiliary module from the top portion of the insert housing.

20 Claims, 13 Drawing Sheets

LIGHT FIXTURE WITH REMOVABLE AUXILIARY LIGHT MODULES

FIELD OF THE INVENTION

The present technology relates to light fixtures including both visible light engines for illuminating an environment, and auxiliary light engines which may emit germicidal light, for example UV germicidal light engines.

BACKGROUND

Reducing pathogens and improving air quality in indoor spaces occupied by many people, for example office buildings, factories, hospitals, nursing homes and schools, may be important to the health of the occupants. One way of reducing pathogens and improving air quality includes the use of germicidal light. Accordingly, there is a need for adding germicidal lights to indoor spaces.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The present technology may relate to a light fixture including a housing defining a channel and an insert lighting module. The insert lighting module may include an insert housing, a visible light engine coupled to a bottom portion of the insert housing for emitting visible light for general illumination, and an auxiliary light module coupled to the insert housing and including an auxiliary light engine for emitting germicidal light effective in deactivating pathogens. A top portion of the insert lighting module, opposite the bottom portion, may be positioned within the channel and the insert lighting module may be coupled to the housing. The auxiliary light module may be uncoupled and removed from the insert housing by performing the steps of: uncoupling the insert lighting module from the housing and removing the insert lighting module from the channel, and with the insert lighting module removed from the channel, uncoupling the auxiliary light module from the insert housing and removing the auxiliary module from the top portion of the insert housing.

In some embodiments, the auxiliary light engine emits ultraviolet germicidal light effective in deactivating pathogens. The auxiliary light engine may emit a dominant wavelength of 222 nm. The auxiliary light engine may be an excimer lamp. The visible light engine may include light emitting diodes.

In some embodiments, the light fixture may include a dosing circuit module electrically coupled to the auxiliary light engine. The dosing circuit module may provide power to and control the auxiliary light engine. The dosing circuit module may not provide power to nor control the visible light engine. The light fixture may also include a visible light driver electrically coupled to the visible light engine to provide power to and control the visible light engine. The visible light driver may be positioned within the housing and not coupled to the insert housing. The dosing circuit module may be coupled to the top portion of the insert housing. The dosing circuit module may control the auxiliary light engine according to a repeating dosing scheme. The dosing scheme may include a first period between 10 seconds and 2 minutes in duration wherein the auxiliary light engine emits the germicidal light followed by a second period between 1 minute and 10 minutes in duration wherein the auxiliary light engine does not emit the germicidal light.

In some embodiments, the auxiliary light module may include a status indicator light. The dosing circuit module may determine an amount of remaining service life of the auxiliary light engine and control the status indicator light to provide different indications corresponding to the remaining service life of the auxiliary light engine. The different indication may include a first indication corresponding to sufficient service life remaining, a second indication corresponding to a predetermine amount of service life remaining, and a third indication corresponding to the service life of the auxiliary light engine being reached. A service life of the visible light engine may be at least twice as long as a service life of the auxiliary light engine. The insert lighting module may be configured so that the auxiliary light module can be replaced when the service life of the auxiliary light engine is reached with a substantially identical second auxiliary light module without replacing the visible light engine in order to operate the light fixture with both germicidal light and visible light beyond the service life of the auxiliary light engine.

In some embodiments, the insert housing may include a first trim portion, a second trim portion, and a central portion between the first trim portion and the second trim portion. The visible light engine may be coupled to the central portion. The first trim portion may define a first aperture and a second aperture. The auxiliary light module may be positioned within the first aperture so that the germicidal light is emitted through the second aperture. The insert housing may also include an optic coupled to central portion and through which the visible light is emitted. The optic may not cover the second aperture so that the germicidal light does not pass through the optic. The second aperture may be smaller than the auxiliary light module so that the auxiliary light module cannot pass through the second aperture. The first trim portion, the second trim portion, and the optic may include curved profiles defining a flush curved bottom surface of the insert lighting module. The light fixture may also include a second auxiliary light module identical to the auxiliary light module, and the second trim portion may define a third aperture and a fourth aperture, wherein the second auxiliary light module is positioned within the third aperture so that germicidal light from a second auxiliary light engine of the second auxiliary light module is emitted through the fourth aperture. The optic may not cover the fourth aperture so that the germicidal light from the second auxiliary light engine does not pass through the optic.

In some embodiments, the light fixture may also include a dosing circuit module coupled to the top portion of the insert housing. The dosing circuit module may be electrically coupled to the auxiliary light engine and the second auxiliary light engine and provide power to and control the auxiliary light engine and the second auxiliary light engine.

In some embodiments, the light fixture may also include an occupancy sensor coupled to the second trim portion, and a visible light driver electrically coupled to the visible light engine and the occupancy sensor. The visible light driver may provide power to and control the visible light engine based on signals from the occupancy sensor.

In some embodiments, the technology may be directed toward a method of replacing the auxiliary light module of a light fixture. The method may include uncoupling the insert lighting module from the housing, with the housing installed in a ceiling, and removing the insert lighting module from the channel, uncoupling the auxiliary light module from the insert housing, with the insert lighting module removed from the channel, and removing the auxiliary module from the top portion of the insert housing, with the auxiliary light module removed, inserting a second auxiliary light module, identical to the auxiliary light module and comprising a second auxiliary light engine, into the top portion of the insert housing and coupling the second auxiliary light module to the insert housing, and positioning the insert housing coupled to the second auxiliary light module within the channel of the housing installed in the ceiling, and coupling the insert lighting module to the housing. The method may also include uncoupling a first dosing circuit module coupled to the top portion of the insert housing, with the insert lighting module removed from the channel, wherein the first dosing circuit module is electrically coupled to the auxiliary light engine and configured to provide power to and control the auxiliary light engine, coupling a second dosing circuit module to the top portion of the insert housing, after uncoupling the first dosing circuit module is removed from the channel, and electrically coupling the second dosing circuit module to the second auxiliary light engine in order to provide power to and control the second auxiliary light engine.

In some embodiments, the technology may be directed toward a method of replacing the insert lighting module of a light fixture. The method may include uncoupling the insert lighting module from the housing, with the housing installed in a ceiling, and removing the insert lighting module from the channel, with the insert lighting module removed from the channel, positioning a second insert housing of a second insert lighting module within the channel of the housing installed in the ceiling, and coupling the second insert lighting module to the housing, wherein the second insert lighting module comprises a second visible light engine coupled to a second bottom portion of the second insert housing and configured to emit visible light for general illumination. The second insert light module may not include any auxiliary light engines configured to emit germicidal light effective in deactivating pathogens.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

FIGS. 1A-1F show views of a light fixture, according to embodiments of the present technology.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Directional references such as "up," "down," "top," "left," "right," "front," and "back," among others are intended to refer to the orientation as illustrated and described in the figure (or figures) to which the components and directions are referencing.

The present technology relates to light fixtures including both a visible light engine for general illumination of a space with visible light, as well as an auxiliary light engine. The auxiliary light engine may include a germicidal light engine for reducing pathogens and improving indoor air quality. An example of a germicidal light engine includes, but is not limited to, a UV light source. Due to the different types of lighting elements and/or different control schemes and/or amount of usage, the service lives of a visible light engine and a germicidal light engine may be significantly different. For example, an LED visible light engine operating under typical working hours use (e.g. 8-12 hours each day in an office building or school) may have a service life of 10-20 years, whereas a non-led germicidal UV light engine operating under an intermittent disinfecting schedule (e.g. 30 seconds on 5 minutes off continuously 24 hours per day) may have a service life of only 5 years. It is disadvantageous to require the replacement of both the visible light engine and the germicidal light engine at a time when only one of the light engines has exceeded its service life. Accordingly, as will be discussed in greater detail below, embodiments of the disclosed light fixtures include features allowing for the auxiliary light engines to be replaced without replacing the visible light engine, and thus allowing the visible light engine to reach its service life before replacement. In some embodiments, the auxiliary light engines may be removed while at least a portion of the light fixture is still installed in a building, for example within a ceiling, and thus provides the advantage of simple field repair/maintenance/upgrade of the light fixture.

Figure 1A:
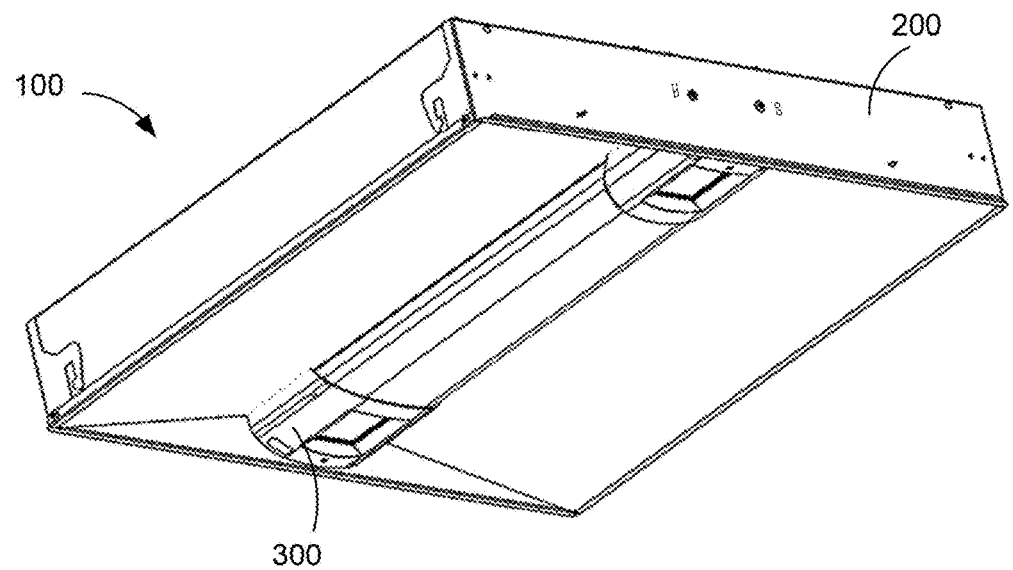
Figure 1B:
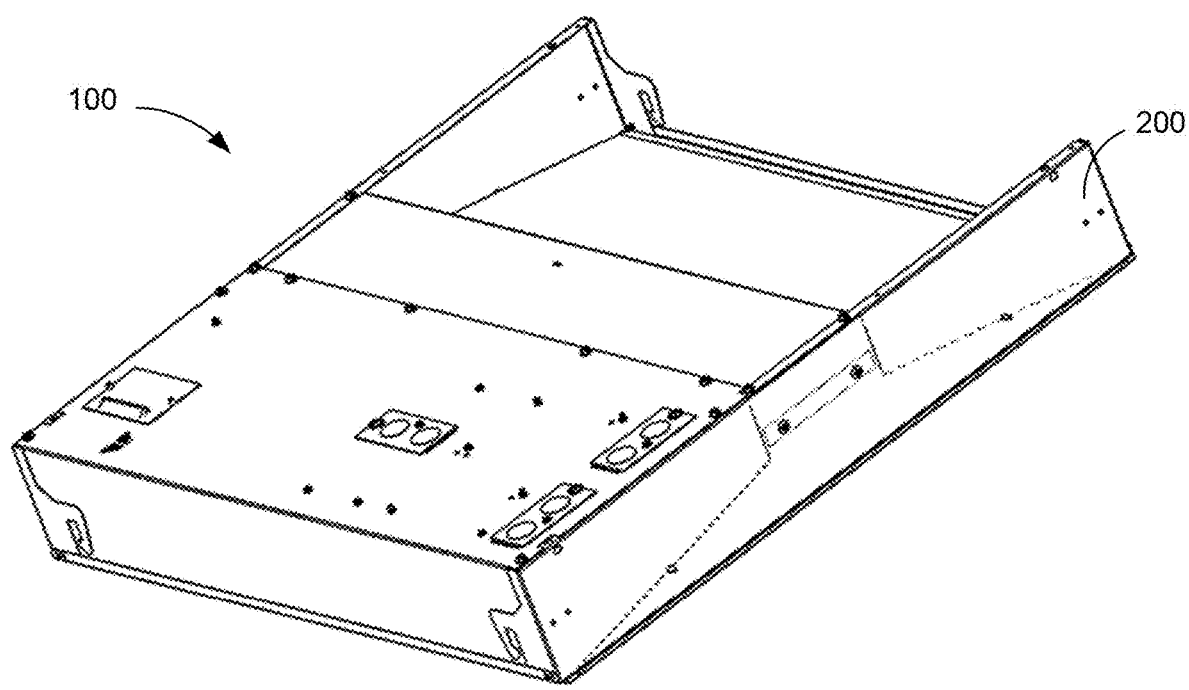

FIG. 1A shows a bottom perspective view of a light fixture 100. As shown, a light fixture 100 may include a housing, for example a reflector housing 200, and an insert lighting module 300. The light fixture 100 may be installed in a building, for example within the ceiling of a building, with the top portion of the light fixture 100, as shown in FIG. 1B, positioned within a ceiling, and the bottom side, also referred to as the light-emitting side, of the light fixture 100, as shown in FIG. 1A, exposed so that light emitted from the insert lighting module 300 illuminates the interior of the building below the light fixture 100. As shown in the bottom view of FIG. 1D, and the side views of FIGS. 1E and 1F, the light fixture 100 may be shaped generally as a rectangular prism. In some embodiments, the light fixture 100 is a recessed light fixture, and may be installed in a T-grid of a dropped ceiling.

Figure 1D:
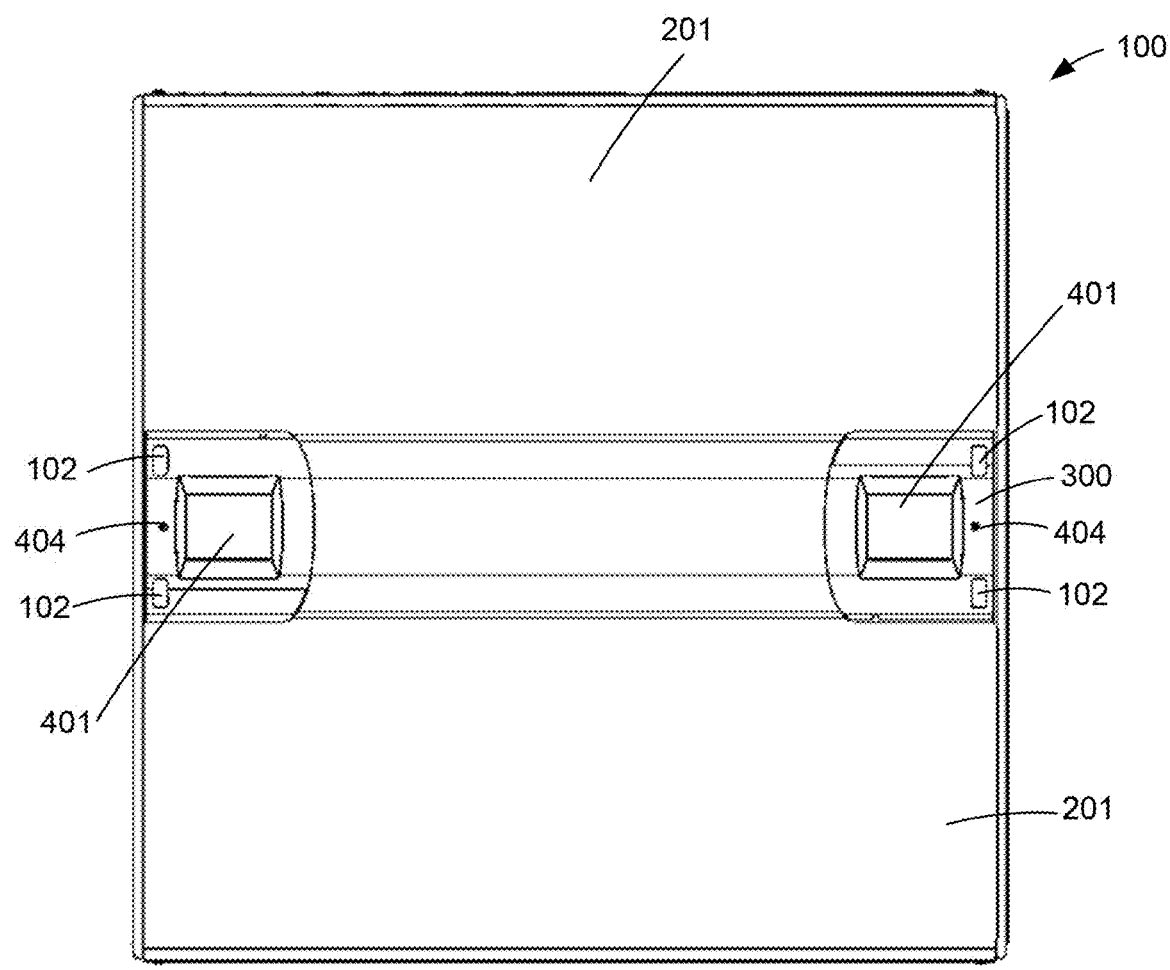
Figure 1E:
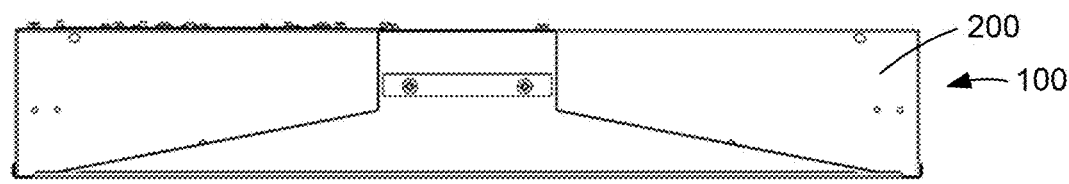
Figure 1F:
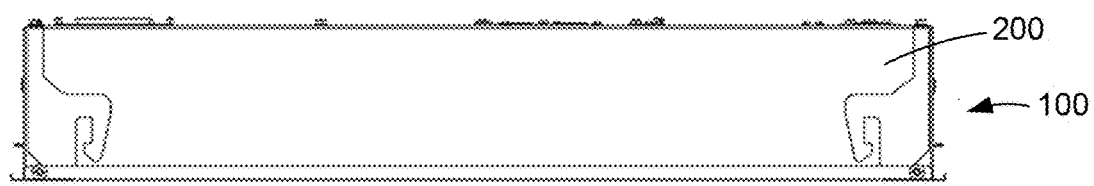
Figure 1G:
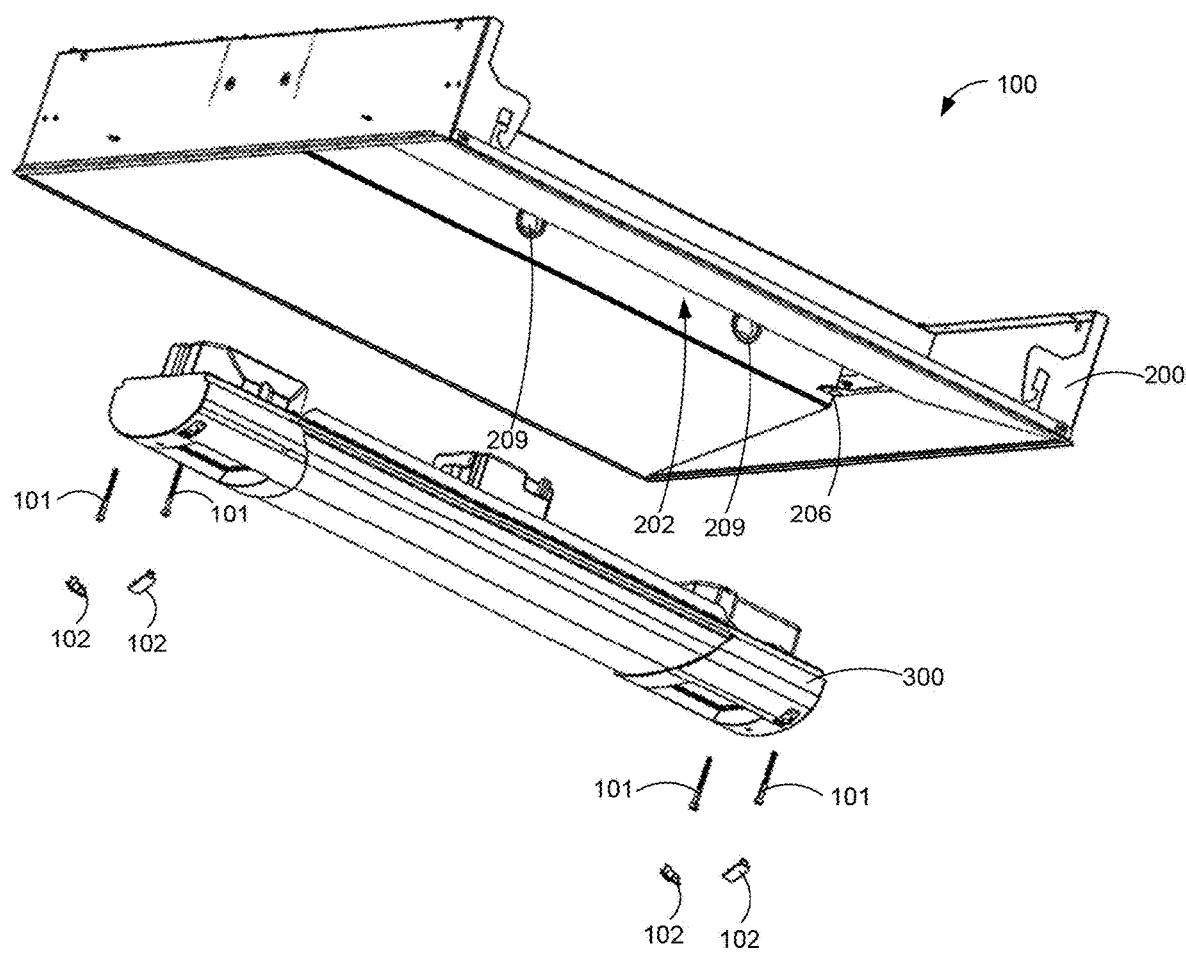
FIG. 1G shows an exploded assembly view of the light fixture of FIGS. 1A-1F, according to embodiments of the present technology.

In some embodiments, an insert lighting module 300 may be positioned within a housing of a light fixture 100. The housing may include reflector surfaces, or may not include reflector surfaces. As shown in the light-emitting side view in FIG. 1D, an insert lighting module 300 may be positioned between two downwardly facing reflector surfaces 201 of a reflector housing 200, so that light emitted from the insert lighting module 300 toward the reflector surfaces 201 is reflected downwardly. In some embodiments, light emitted from an insert lighting module 300 coupled a housing without reflector surfaces may be emitted downwardly from the housing. In some embodiments, an insert lighting module 300 may be removed from a housing, for example but not limited to a reflector housing 200, from a light emitting side of the light fixture 100. For example, FIG. 1G shows an exploded view of a light fixture 100, and as shown, the insert lighting module 300 may be removed from the reflector housing 200 from the light emitting side. Further as shown, the insert lighting module 300 is positioned within, and can be removed from, a channel 202 of the reflector housing 200.

Figure 2A:
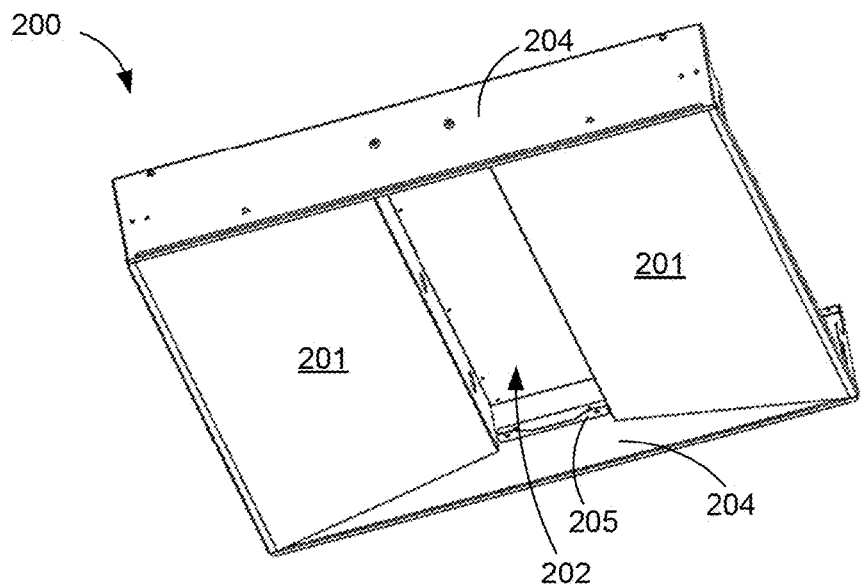
FIGS. 2A-2C show views of a reflector housing of a light fixture, according to embodiments of the present technology.
Figure 2B:
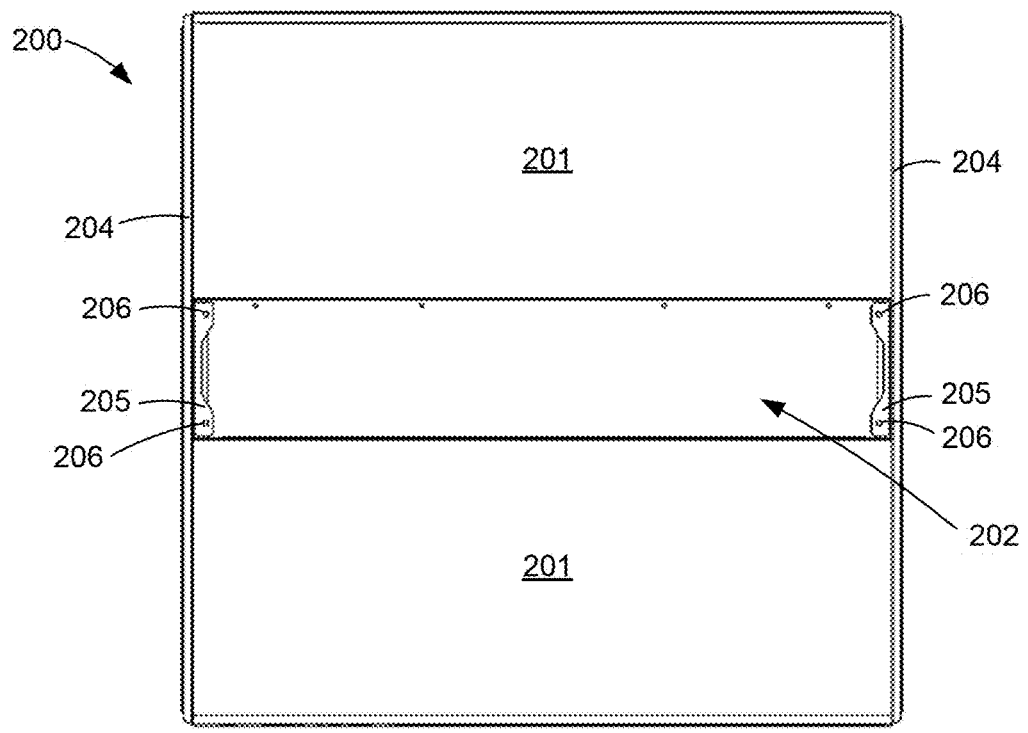
Figure 2C:
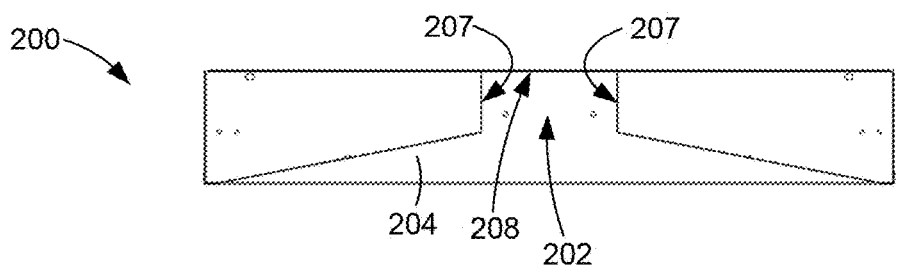

FIGS. 2A-2C show views of a reflector housing 200. As shown, the reflector housing 200 includes a channel 202 between the two reflector surfaces 201 and two sidewalls 204 of the reflector housing 200. The channel 202 may be generally a rectangular prism in shape with an open bottom side. As shown in the cross-sectional view of FIG. 2C, the channel 202 may be defined by a top surface 208, two side surfaces 207, the two sidewalls 204, and an open bottom side through which the insert lighting module 300 is received. The channel 202 is shaped and sized to correspond to the shape and size of the insert lighting module 300 so that at least of portion of the insert lighting module 300 may be positioned within the channel 202 and coupled to the reflector housing 200. The reflector housing 200 may include tabs 205 extending from the sidewalls 204 into the channel 202, as shown for example in FIGS. 2A and 2B. The tabs 205 may include holes 206 for receiving fasteners 101, as shown in FIG. 1G, for coupling the insert lighting module 300 to the reflector housing 200. As shown in FIG. 1G, the fasteners 101 extend through the insert lighting module 300 from below so that the insert lighting module 300 may be uncoupled from the reflector housing 200 and removed from the channel 202 while the reflector housing 200 is still installed within the ceiling of a building. This is advantageous in allowing repair/maintenance/upgrade of portions of a light fixture 100 without uninstalling the entire light fixture 100, which reduces the time and costs of performing a repair/maintenance/upgrade.

In some embodiments, the reflector housing 200, including the reflector surfaces 201, the surfaces of the channel 202, the sidewalls 204, and tabs 205, may be comprised of one or more pieces of material, for example one or more pieces of die-formed sheet metal coupled together. The reflector housing 200 may include surface coatings, for example the reflector surface 201 may be coated with a matte reflective finish for diffusion of light emitted from the insert lighting module 300.

Figure 3A:
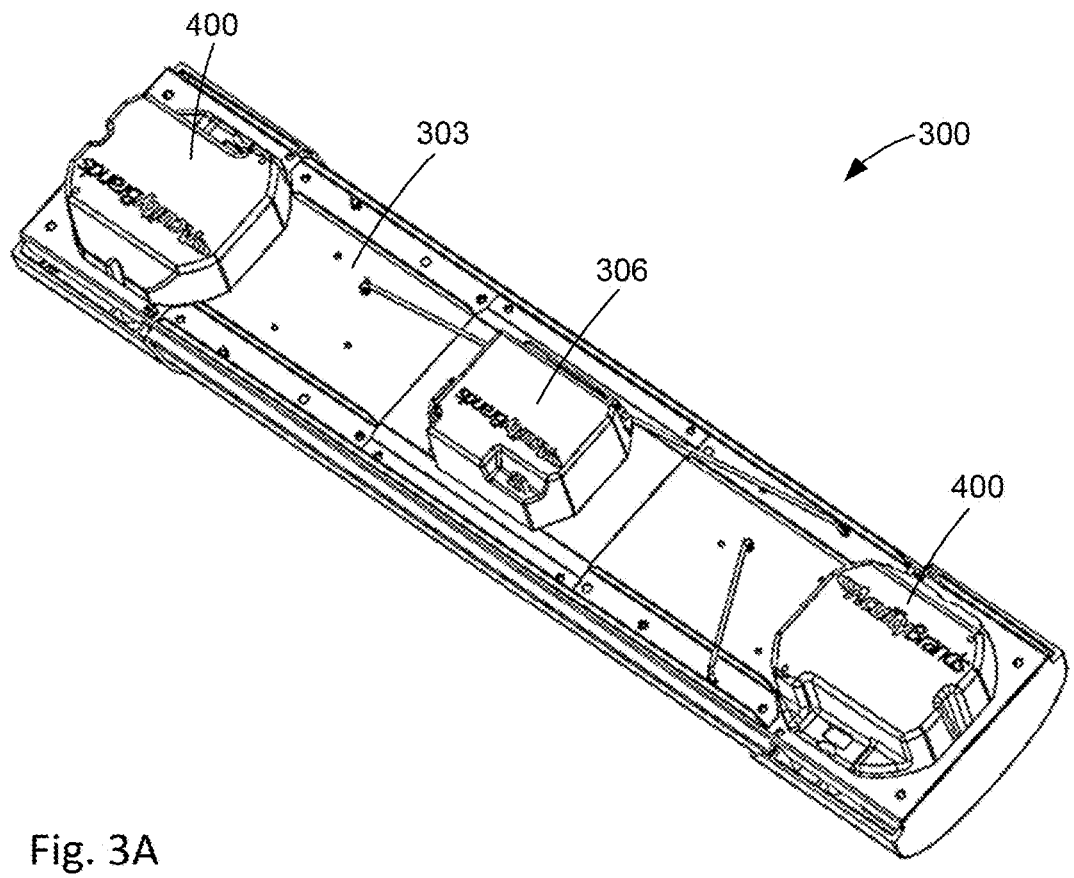
FIGS. 3A-3G show views of an insert lighting module of a light fixture, according to embodiments of the present technology.
Figure 3B:
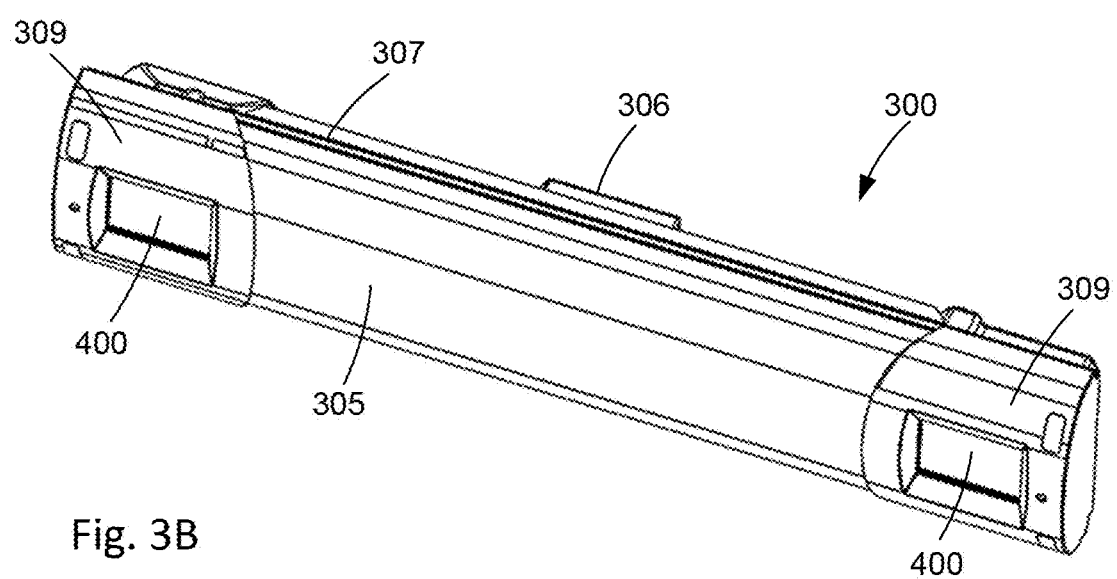

FIGS. 3A and 3B show a top perspective view and a bottom perspective view, respectively, of an insert lighting module 300. The top portion 301 of the insert lighting module 300, as shown in the side view FIG. 3D, may be referred to as the mounting portion due to the top portion 301 being the portion of the insert lighting module 300 which can be received within the channel 202 of the reflector housing 200. The top portion 301 may include wiring, electrical components, and mounting hardware which is received within the channel 202 and thus not visible to an observer below the light fixture 100 while the light fixture 100 is in an installed/operational configuration, as shown in FIG. 1A.

The bottom portion 302 of the insert lighting module 300, as shown in the side view FIG. 3D, may be referred to as the light emitting portion due to the bottom portion 302 being: the portion of the insert lighting module 300 which is not received within the channel 202 of reflector housing 200, the portion visible to an observer from below the light fixture 100 when the light fixture 100 is in an installed/operational configuration, as shown in FIG. 1A.

Figure 5:
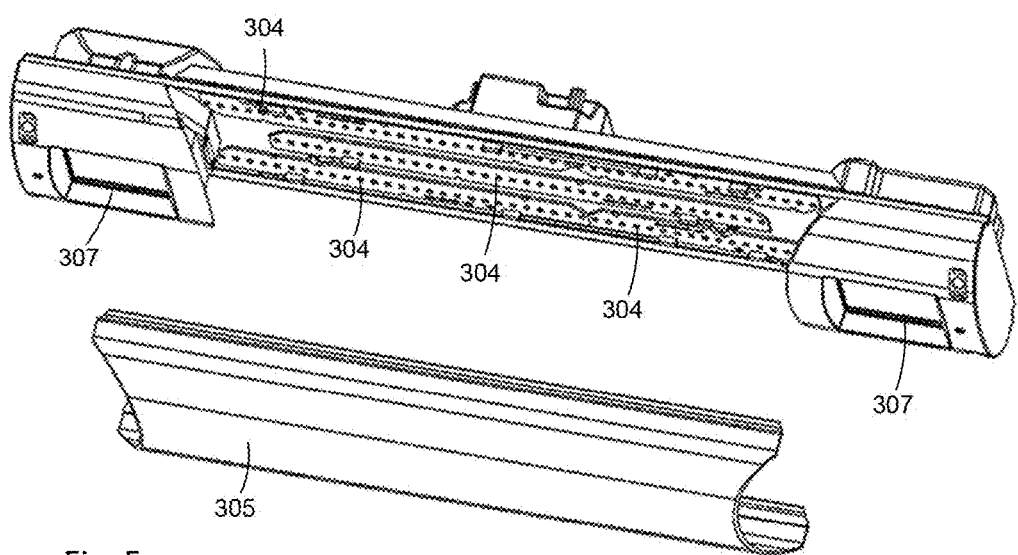
FIG. 5 shows an exploded view of an insert lighting module with the optic removed showing the visible light engines, according to embodiments of the present technology.

The insert lighting module 300 may include an insert housing 303, one or more visible light engines 304, one or more optics 305, one or more auxiliary lighting modules 400, and one or more dosing circuit module 306. As shown in FIG. 5, the one or more visible light engines 304 may be coupled to the insert housing 303 on the bottom portion 302 of the insert lighting module 300 and covered by the optic 305 coupled to the housing 303. Light emitted from the visible light engines 304 may be diffused through the optic 305, and light emitted from the auxiliary lighting module 400 may not be diffused through the optic 305. The optic 305 can be made of any non-metallic material that permits light to exit through the optic 305, including, but not limited to, polymeric materials, glass, silicone and various other suitable materials for light distribution.

The visible light engines 304 may comprise one or more PCBs populated with LEDs for generating and emitting light, or may be chip-on-board LEDs provided directly on the insert housing 303. In some embodiments, the visible light engine 304 may receive power and/or control signals from one or more visible light drivers 902, as will be discussed below. In some embodiments, the visible light engines 304 may be driverless, for example a driverless LED system. The visible light drivers 902 may be for example an LED driver coupled to the insert housing 303 and/or the reflector housing 200. The LEDs may be various types of LEDs including single-die LEDs, multi-die LEDs, direct current (DC) LEDs, alternating current (AC) LEDs, organic light emitting diodes, and/or various other suitable LEDs. White, color, or multicolor LEDs may be used. Moreover, the LEDs need not all be the same color and/or type; rather, mixtures of different colors and/or types of LEDs may be used.

Figure 4A:
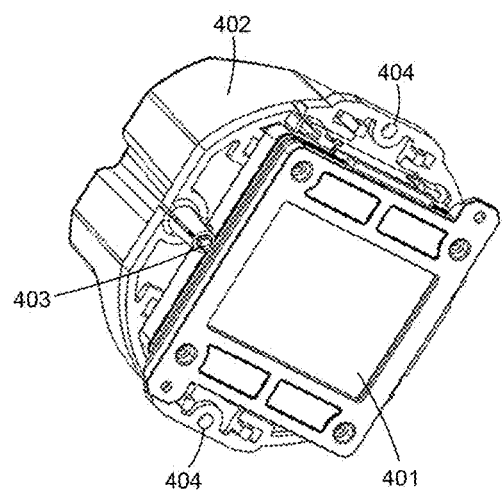
FIGS. 4A and 4B show views of an auxiliary lighting module of an insert lighting module of a light fixture, according to embodiments of the present technology.
Figure 4B:
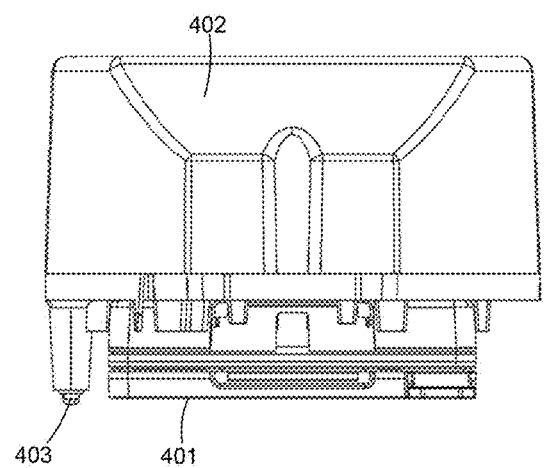

The auxiliary lighting modules 400 may include an auxiliary light engine coupled to a housing 402, for example as shown in FIGS. 4A and 4B. The auxiliary light engine 401 may emit visible, IR (invisible), UV (invisible) or a combination therefore. The light emitted from the auxiliary light engine 401 may be germicidal light, and may not provide general illumination light. The germicidal light may be effective in deactivating pathogens. Pathogens include, but are not limited to: micro-organisms, bacteria, viruses, and spores. The germicidal light may deactivate the pathogens, for example, by rupturing the cell membrane or breaking apart a DNA chain or RNA chain in the pathogen.

The frequency spectrum of the auxiliary light engine may have dominant wavelengths in the ultraviolet range with wavelengths between 200 nm and 400 nm. The dominant wavelength(s) emitted by the auxiliary light engine 401 may be selected in order to deactivate specific pathogen(s) upon exposure to a predetermined dosage. The dominant wavelength(s) may also be selected in order to minimize harmful side effects to humans. In some embodiments, the dominant wavelength of the auxiliary light engine is 222 nm, which has been found to deactivate pathogens while also being safe for human exposure. In some embodiments, the auxiliary light engine may be an excimer lamp. The excimer lamp may include Xenon monochloride (KrCl) as a working excimer molecule producing a dominant wavelength of 222 nm.

The dosage of the germicidal light may be controlled by the dosing circuit module 306 electrically coupled to the auxiliary light engine 401. For example, dosing circuit module 306 may include a dosing scheme, also referred to as a disinfecting schedule, wherein the auxiliary light engine 401 is turned on to emit germicidal light for a first period followed by a second period wherein the auxiliary light engine 401 is turned off. In some embodiments, the first period may be 10 seconds to 2 minutes, and the second period may be 1 minute to 10 minutes. For example, the first period may be 20 seconds and the second period may be 5 minutes. The dosing circuit module 306 may be configured to run the dosing scheme continuously, i.e. 24 hours a day, so that the auxiliary light engine 401 is repeatedly turned on for the first period and turned off during the second period. The dosing circuit module 306 may include a processor and storage for recording the total time the auxiliary light engine 401 is on in order to determine when the auxiliary light engine 401 is nearing or has reached its service life.

The dosing scheme of a dosing circuit module 306 may be selected based on a combination of one or more of: the total number of auxiliary light engines 401 in a room, the height of the auxiliary light engines above the floor of the room, the duration of exposure needed to deactivate a desired pathogen, and/or the maximum safe dosage for human exposure of the dominant wavelength(s) emitted by the auxiliary light engine 401.

As shown in FIGS. 4A and 4B, an auxiliary light module 400 may further include a status light 403 adjacent to the auxiliary light engine 401. The status light 403 may include an LED, and may be a multi-color LED. The status light 403 may be visible through an opening in the trim portion 309 as shown in FIG. 1D. The status light 403 may be electrically connected to circuitry, for example the dosing circuit module 306, in order to be illuminated to provide the status of the auxiliary light engine 401. For example, the status light 403 may be illuminated a first color, e.g. green, to indicate that power is provided to the system of the auxiliary light engine 401 and the dosing circuit module 306 and that the dosing circuit module 306 is running the dosing scheme. If the status light 403 is not illuminated, this may indicate that the auxiliary light module 400 is not receiving power and therefore is not deactivating pathogens. Further for example, the status light 403 may be illuminated a second color, e.g. yellow, to indicate that the dosing circuit module 306 has determined that the auxiliary light engine 401 is within a predetermined duration of remaining service life, e.g. 1 month of service life left. Further for example, the status light 403 may be illuminated a third color, e.g. red, to indicate that the dosing circuit module 306 has determined that the auxiliary light engine 401 has reached the end of its service life, and should be replaced as the auxiliary light engine 401 may soon no longer emit any light or may have reduced power and no longer be effective in deactivating pathogens.

In some embodiments, the dosing circuit module 306 may be configured to no longer turn on the auxiliary light engine 401 when the service life of the auxiliary light engine 401 is reached, and may be configured so that a service life duration counter cannot be reset. This configuration is beneficial in preventing an auxiliary light engine 401 which may no longer be effective in deactivating pathogens from being used further.

In some embodiments, the light fixture 100 may include any number of auxiliary lighting modules 400, including zero, one, two, three, or four or more. The number of auxiliary lighting modules 400 may be selected based on a combination of one or more of, the size of the room, the height of the light fixture from the floor, the number of light fixtures, and/or the number of light fixture including one or more auxiliary lighting modules. In some embodiments, a room may include a plurality of light fixtures 100, wherein the plurality of light fixtures 100 may include light fixtures having different numbers (e.g. 0, 1, 2, 3, etc.) of auxiliary lighting modules 400 in order for the room to have a predetermined total number of auxiliary lighting modules 400.

Figure 3C:
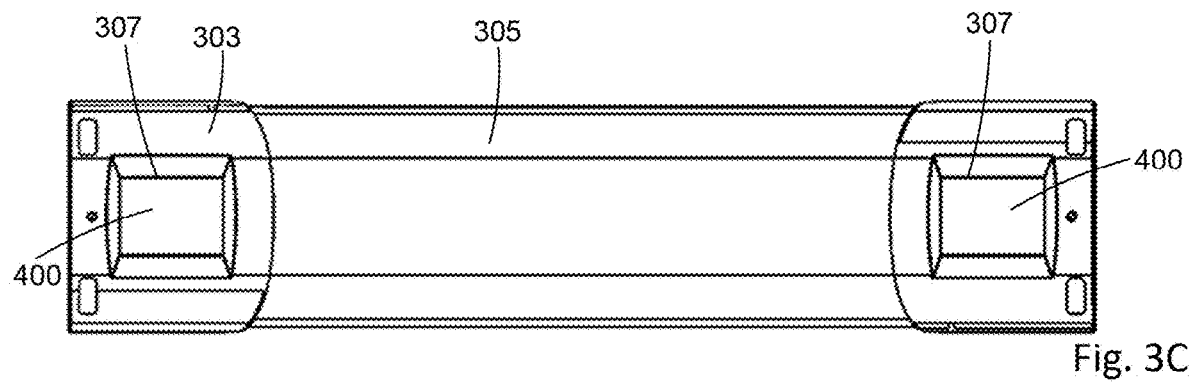
Figure 3D:
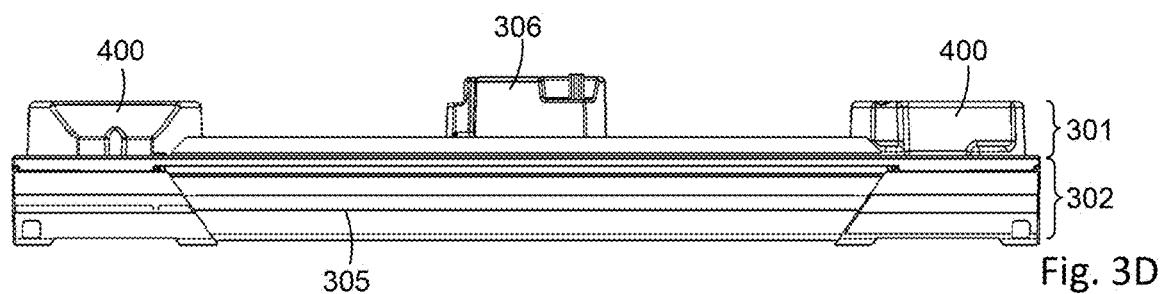
Figure 3E:
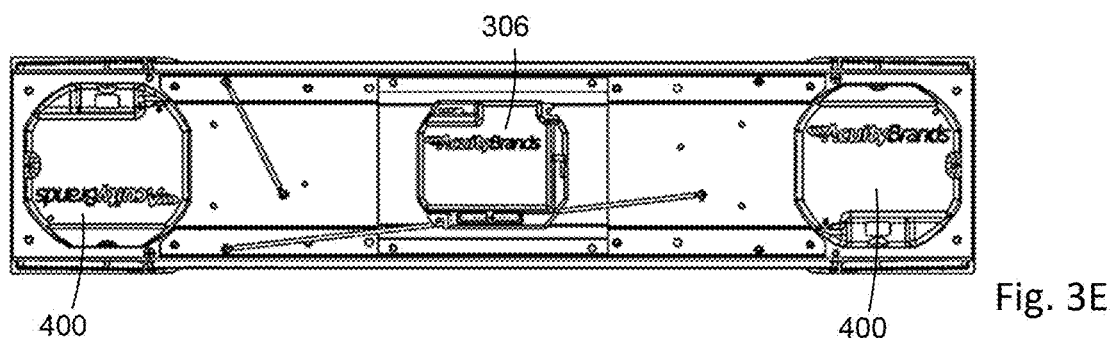
Figure 3F:
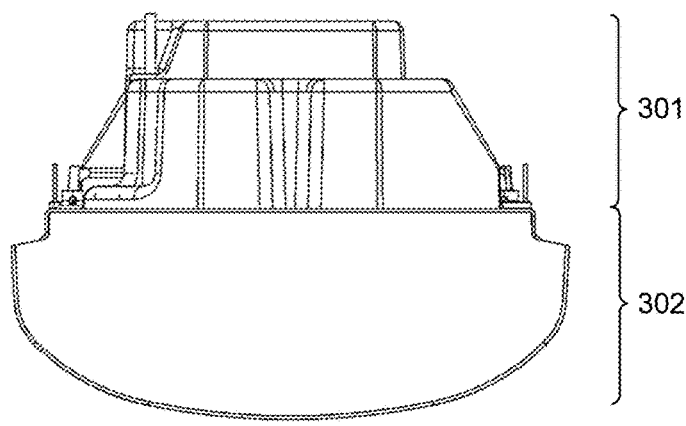

As shown in the bottom view of FIG. 3C and side view of FIG. 3D, an insert lighting module 300 may include two auxiliary lighting modules 400 coupled to the insert housing 303 and positioned on opposite sides of the optic 305, and therefore positioned on opposite sides of the visible light engines 304. As shown in FIGS. 3D and 3E, in some embodiments, a dosing circuit module 306 may be coupled to the insert housing 303, and may be electrically coupled to one or more auxiliary lighting modules 400 in order to provide electrical control signals and power to the auxiliary lighting modules 400. In some embodiments, the auxiliary lighting modules 400 and the dosing circuit modules 306 may be replaced at the same time and in some embodiments the auxiliary lighting modules 400 may be replaced with new auxiliary lighting modules 400 and the new replacement auxiliary lighting modules 400 may be electrically coupled to an un-replaced dosing circuit module 306. In some embodiments, a dosing circuit module 306 may be included in the auxiliary lighting modules 400 in order to provide electrical control signals and power to other components within the auxiliary lighting modules 400.

Figure 6:
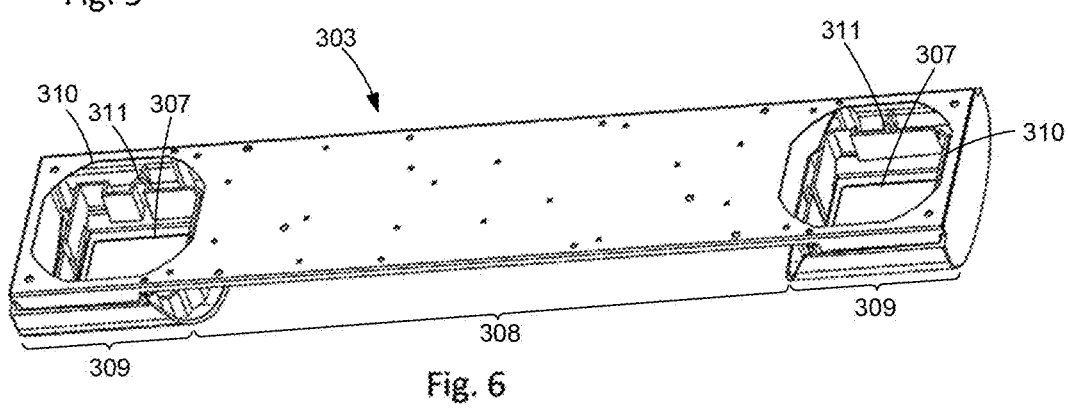
FIG. 6 shows a mounting side view of an insert housing of an insert lighting module, according to embodiments of the present technology.

The auxiliary light module 400 and insert housing 303 include features allowing the auxiliary light module 400 to be inserted and removed from the insert housing 303 from the top side of the insert housing 303. FIG. 6 shows a top side view of an insert housing 303. As shown, the insert housing 303 may include a central portion 308 and two trim portions 309 on opposite ends of the central portion 308. As shown in FIG. 5, the visible light engines 304 are coupled to the bottom side of the central portion 308, and the optic 305 is coupled, for example with a snap-fit, to the central portion 308 between the trim portions 309 so that the optic 305 does not cover the apertures 307 defined in the trim portions 309 so that germicidal light emitted from the auxiliary light engines 401 is not rendered ineffective due to passing through the optic 305. As shown in FIG. 3D, the trim portions 309 and the optic 305 may have substantially similar curved profiles forming a substantially flush curved surface along the bottom side of the insert lighting module 300.

The insert housing 303 may further define mounting apertures 310 in the trim portions 309, as shown for example in FIG. 6. The mounting apertures 310 are sized and shaped to receive the housing 402 of the auxiliary lighting modules 400 from the top side of the insert housing 303, as shown for example in FIGS. 3A and 3G. The auxiliary lighting modules 400 may be coupled to the insert housing 303 with fasteners extending through mounting holes 404 of the housing 402 into mounting holes 311 of the insert housing 303.

As shown in FIGS. 3A and 3B, the housing 402 is positioned within the mounting apertures 310 and coupled to the insert housing 303 so that auxiliary light engine 401 are aligned with and can emit germicidal light through the apertures 307 of the insert housing 303.

As noted above, the ability to remove the auxiliary light module 400 from the insert lighting module 300, which includes the visible light engine(s) 304, is beneficial with light engines that have significantly different service lives, for example a difference of 2× or more. For example, a visible light engines 304 with a 10 year service life can be used its entire service life using auxiliary light modules 400 with 5 year service lives, by replacing the auxiliary light module 400 with a new auxiliary light module 400 5 years into the use of the visible light engines 304.

Figure 3G:
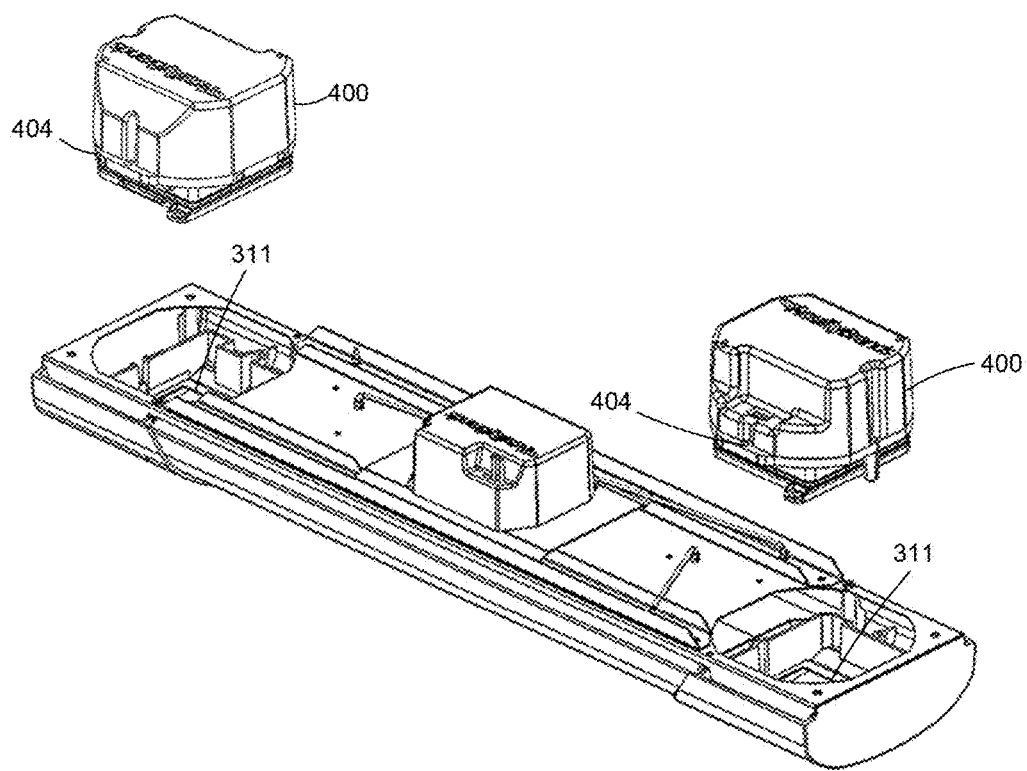

To replace an auxiliary light modules 400 of an insert lighting module 300 according to the present technology, the insert lighting module 300 may first be uncoupled from the reflector housing 200 by removing trim plugs 102 covering the fasteners 101 extending through the trim portions 309 into the holes 206 of the tabs 205, as shown in FIG. 1G. With the fasteners 101 removed, the insert lighting module 300 may be removed from the light emitting side of the light fixture 100 with the reflector housing 200 still installed in the ceiling. Next, fasteners extending through holes 404 into holes 311 may be removed in order to uncouple the auxiliary light modules 400 from the insert housing 303, so that the auxiliary light modules 400 may be pulled out of the mounting apertures 310, as shown in FIG. 3G.

With the used auxiliary light modules 400 removed, a new set of auxiliary light modules 400 may be installed by reversing the removal process. Specifically, a new set of auxiliary light modules 400 may be placed within the mounting apertures 310 and fasteners may be extended through holes 404 into holes 311 to couple the auxiliary light modules 400 to the insert housing 303.

While the insert lighting module 300 is removed for replacement of the auxiliary light modules 400, the dosing circuit module 306 may also be uncoupled from the inserting housing 303 and replacement with a new dosing circuit module 306.

The new auxiliary light modules 400 and new dosing circuit module 306 may be electrically connected to each other and to power and control wiring extending from the reflector housing 200 prior to reinserting the insert lighting module 300 back into the channel 202.

To recouple the insert lighting module 300 to the reflector housing 200, the lighting module 300 may be inserted into the channel 202, and the fasteners 101 may be extended through the trim portions 309 and into the holes 206 of the tabs 205. This may be followed by covering the openings in the trim portions 309 with the trim plugs 102, as shown in FIG. 1D.

Figure 7A:
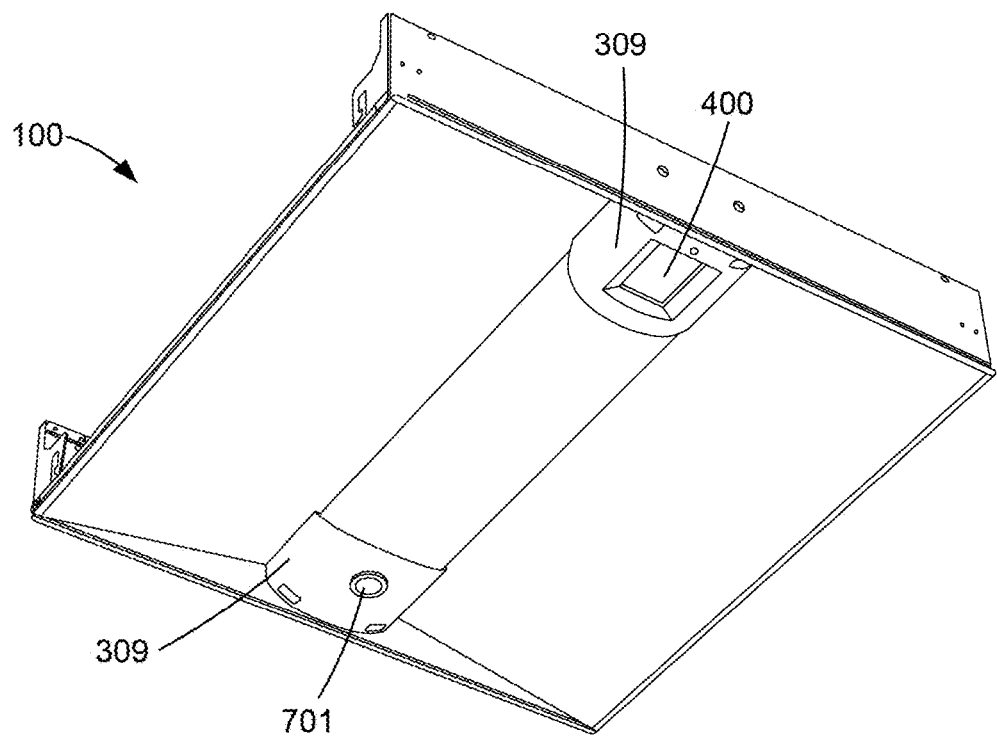
FIG. 7A shows a light fixture including an auxiliary lighting module and a sensor module, according to embodiments of the present technology.
Figure 7B:
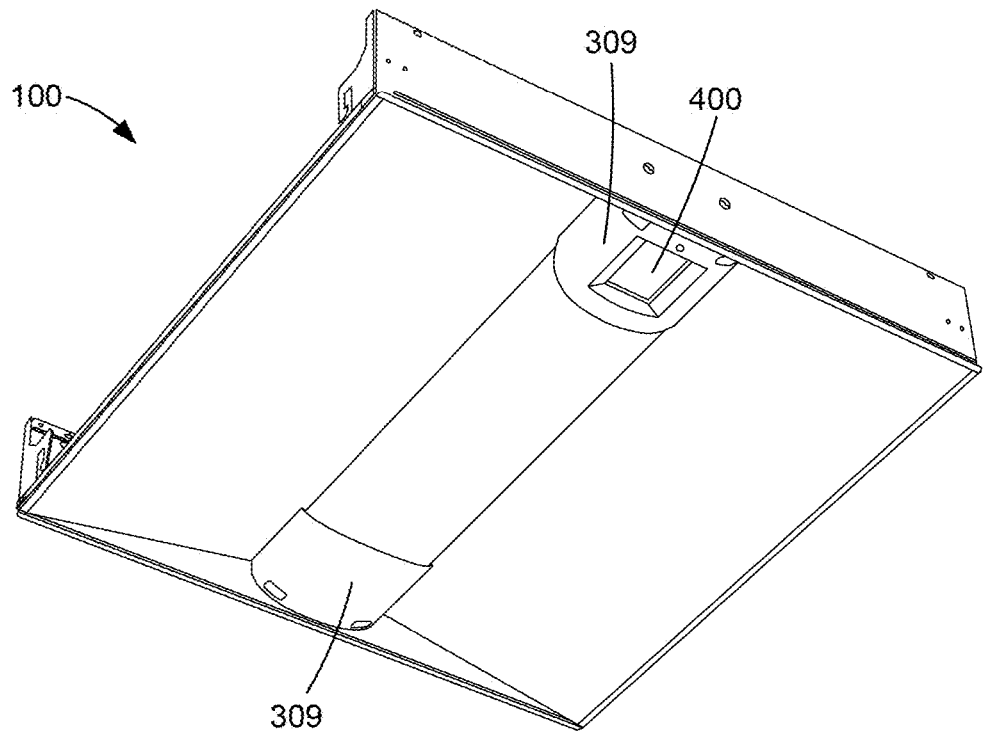
FIG. 7B shows a light fixture including an auxiliary lighting module and a module-less trim portion, according to embodiments of the present technology.

In some embodiments, an insert lighting module 300 may include trim portions 309 without a corresponding auxiliary light module 400. For example, as shown in FIG. 7A, a light fixture 100 may include an insert lighting module 300 having an auxiliary light module 400 at one end of the insert lighting module 300 and a sensor 701 coupled to the trim portion 309 at the other end of the insert lighting module 300. The sensor 701 may be an occupancy sensor, and may be electrically coupled to a driver of the visible light engine 304 and used as an input to determine when to turn the visible light engine 304 on or off. In some embodiments, the sensor 701 may be provided as an input to the dosing circuit module 306 in order to control dosing of the auxiliary light engine. In some embodiments, a sensor 701 may be included in an auxiliary light module 400. Further, in some embodiments, for example as shown in FIG. 7B, a light fixture 100 may include an auxiliary light module 400 at one end of the insert lighting module 300 and a trim portion 309 without a light engine or sensor, i.e. a module-less trim portion 309, at the other end of the insert lighting module 300. Light fixtures 100 with only one auxiliary light module 400 may be used, for example, in a germicidal dosing scheme where two auxiliary light modules 400 over a certain area would result in too much exposure to UV radiation of the occupants of the room. In some embodiments, the above noted steps for removing and coupling an insert lighting module 300 to a reflector housing may be used to replace a first insert lighting module 300 with a second an insert lighting module 300 having a different configuration of trim portions 309 including trims portions 309 with auxiliary light modules 400 or sensors 701, as well as module-less trim portions 309.

Figure 8A:
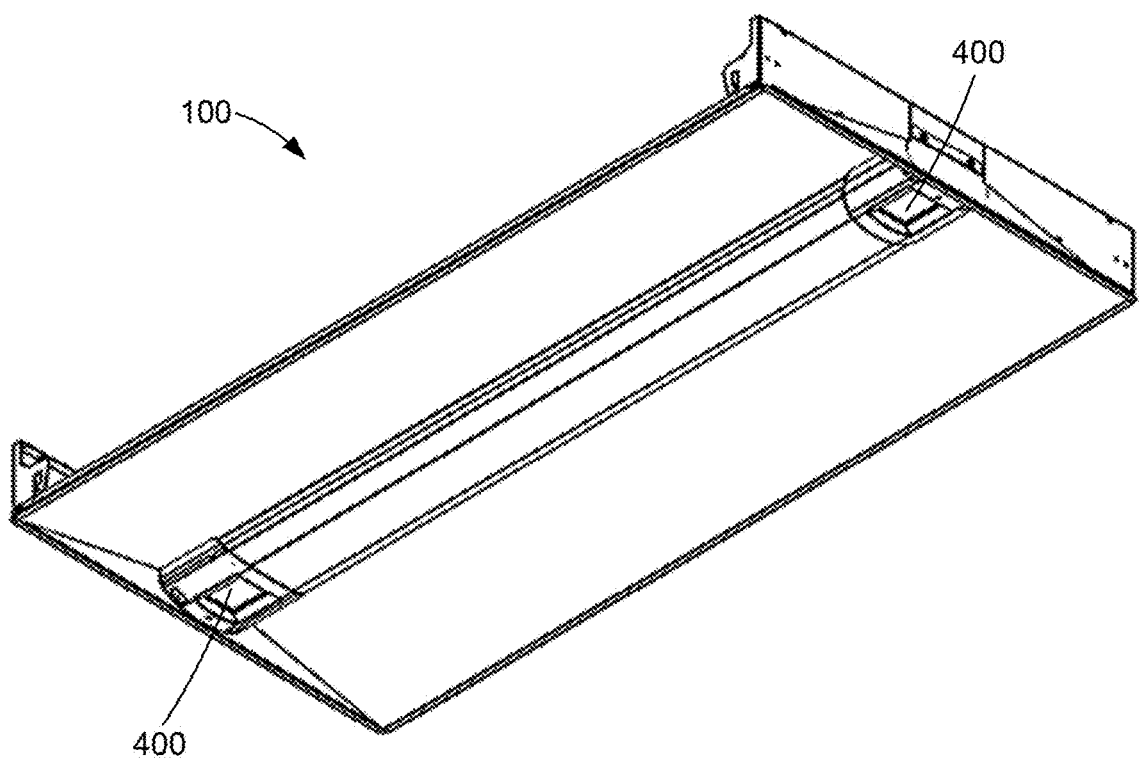
FIGS. 8A and 8B show light fixtures similar to the light fixtures of FIGS. 1A and 7A with different form factors, according to embodiments of the present technology.
Figure 8B:
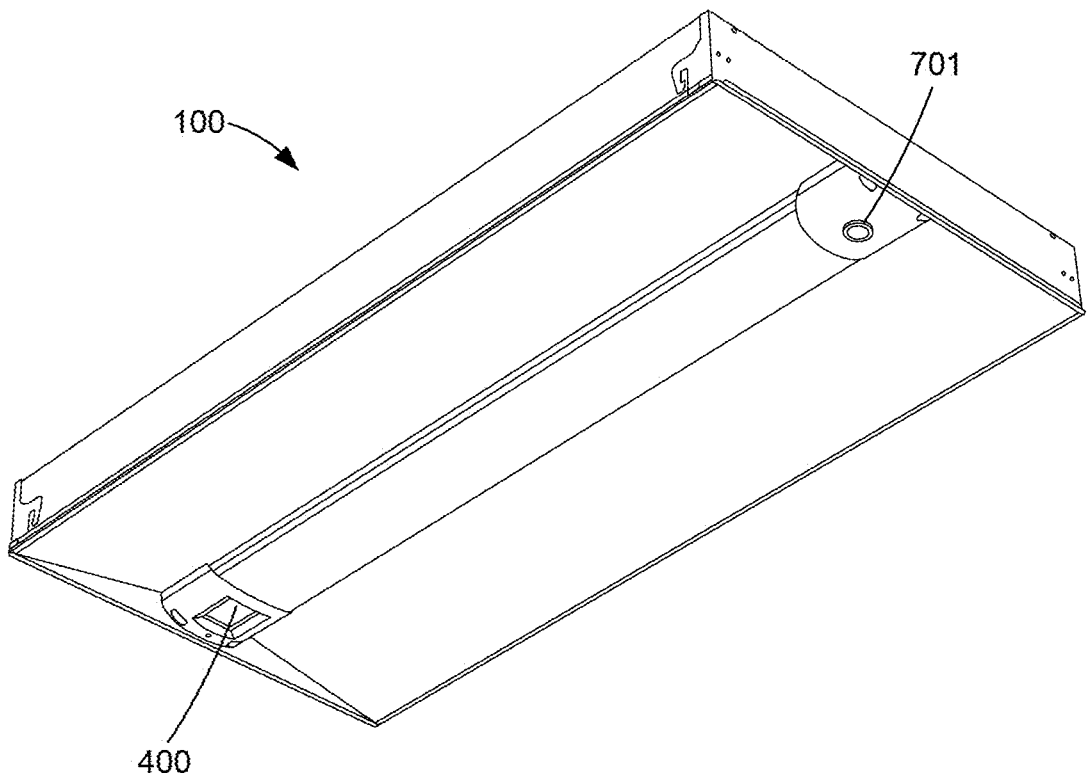

It will be appreciated that the shape, configuration, and components of the light fixture 100 should not be considered limiting on the present disclosure as the light fixture 100 may have any desired shape or configuration. The light fixtures 100 in FIGS. 1A-1G and 7A and 7B have a generally square bottom profile, however some in embodiments, the bottom profile can be any shape or form factor. For example, as shown in FIGS. 8A and 8B, a light fixture 100 may have an elongated rectangle bottom profile. When used in a dropped ceiling, elongated rectangle light fixtures 100 may occupy two grid squares, whereas square light fixtures 100 may occupy one grid square. In some embodiments, the bottom profile of a light fixture 100 may be: 1'×2', 1'×4', 2'×2', 2'×4', 20"×4', 300 mm×1200 mm, 500 mm×1200 mm, 600 mm×1200 mm, or 600 mm×600 mm.

Figure 9:
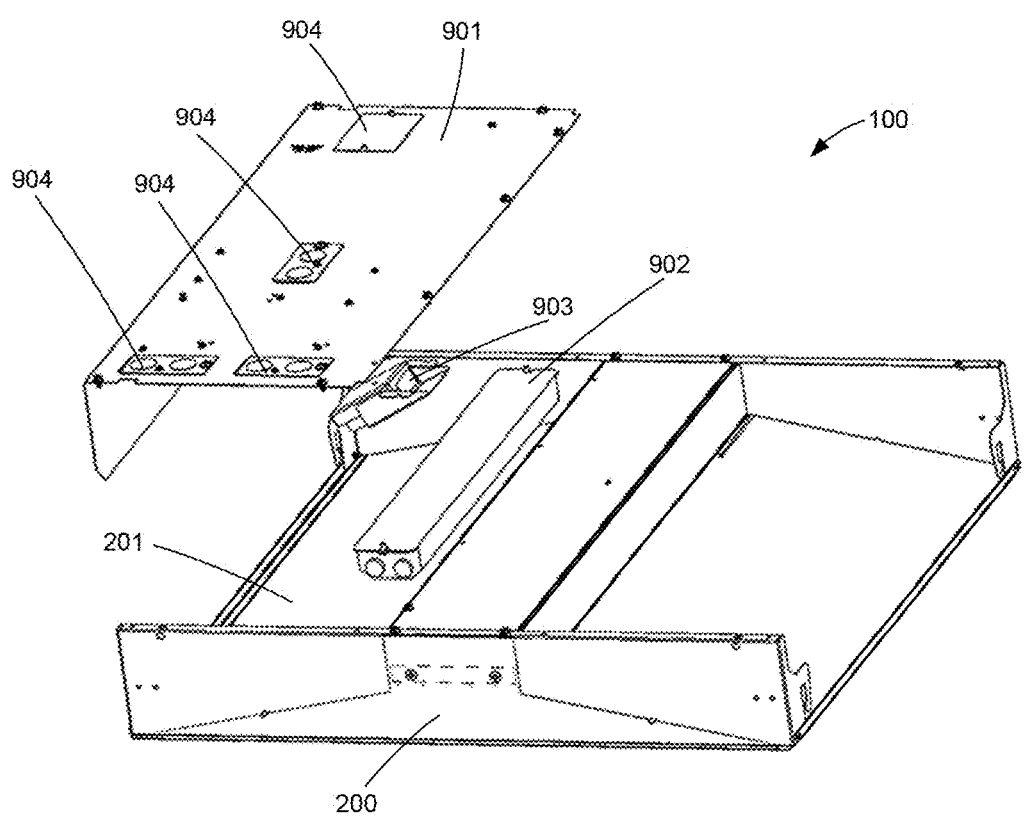
FIG. 9 shows a top side view of a light fixture, according to embodiments of the present technology.

In some embodiments, the reflector housing 200 may house various electrical components of a light fixture 100. FIG. 9 shows a top view of a light fixture 100 with a top panel 901 removed from the reflector housing 200. The top panel 901 may include openings 904 for cables providing power and/or control signals to a visible light driver(s) 902 and a dosing circuit module(s) 306, in order to control and illuminate the visible light engine(s) 304 and auxiliary light engine(s) 401. In some embodiments, a visible light driver 902 may be positioned within a cavity defined by the reflector housing 200 between a reflector surface 201 and a top panel 901, as shown in FIG. 9. The visible light driver 902 may be electrically coupled to the visible light engines 304 with cables (omitted for clarity) extending through openings 209, as shown in FIG. 1G, in a side surface 207 of the channel 202. Cables for providing power and/or control of the dosing circuit module(s) 306 may also extend through the openings 209. In some embodiments, a light fixture 100 may further include a network connection 903, e.g. a CATS outlet, for receiving signals from a remote computer network to control the visible light driver 902. In some embodiments, the fixture may additionally include batteries positioned within the reflector housing 200 for providing backup power to the visible light driver 902 in a case of a power interruption.

Figure 10A:
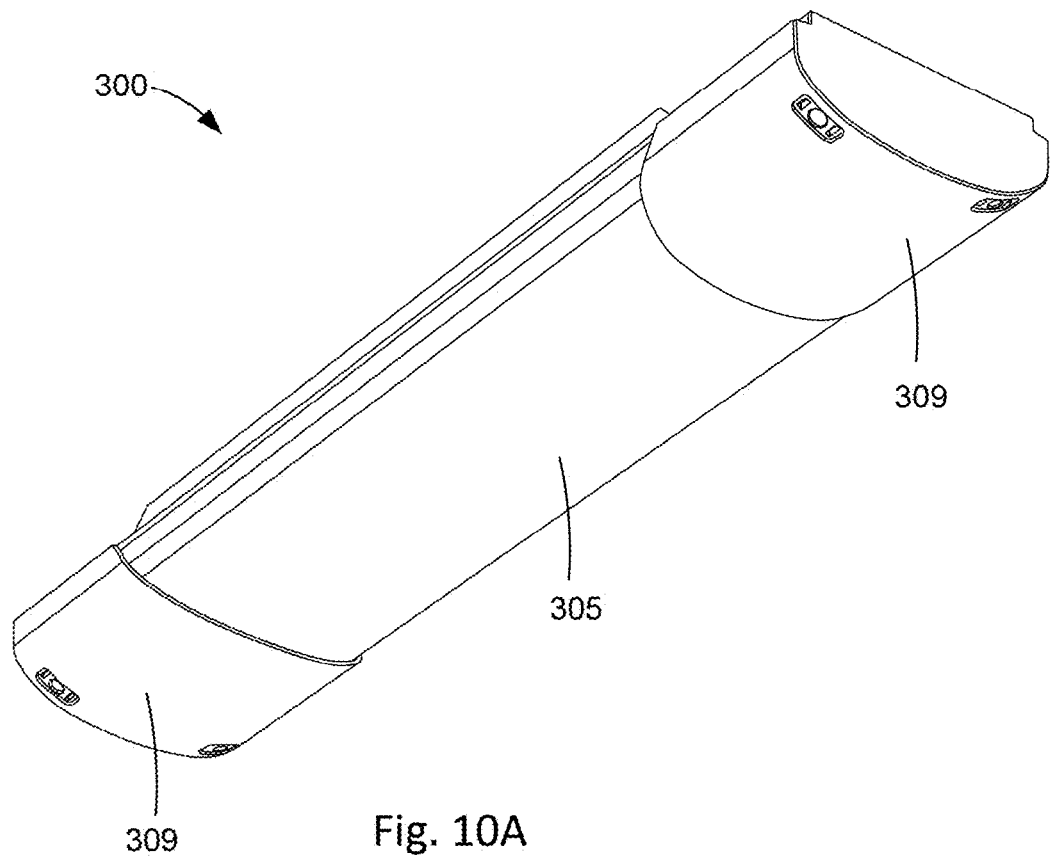
FIGS. 10A and 10B show a lighting module insert not including auxiliary lighting modules, according to embodiments of the present technology.
Figure 10B:
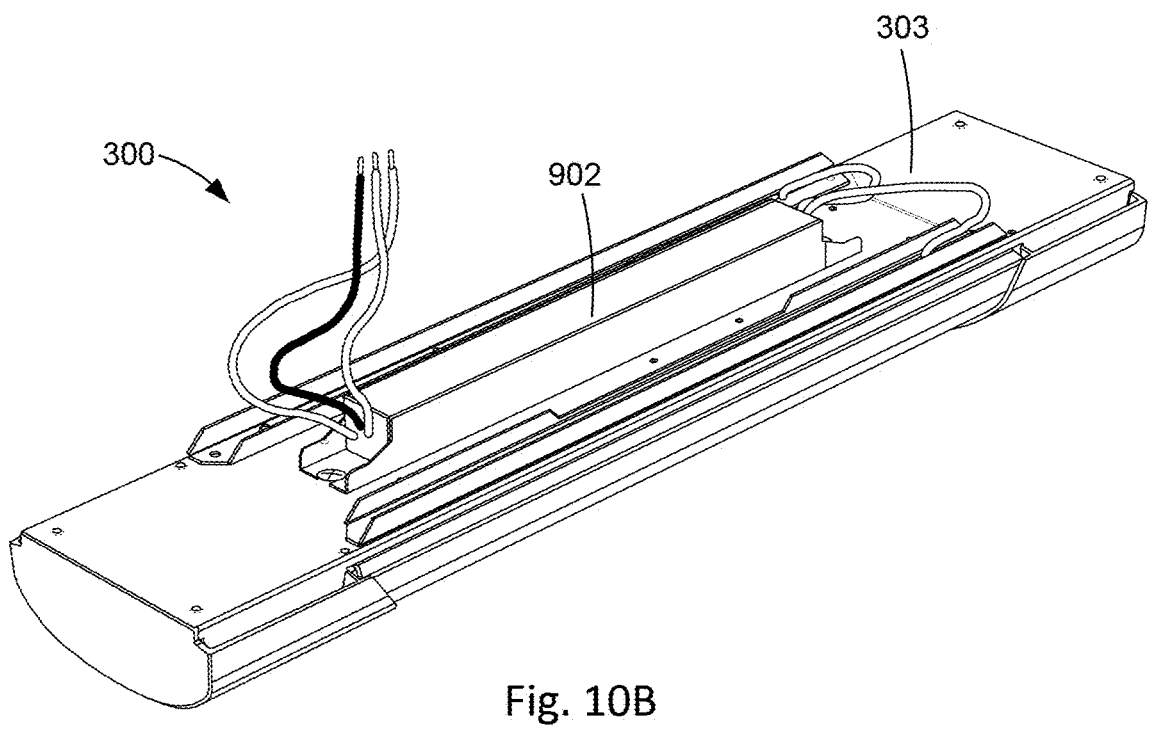

As noted above, in addition to removing an insert lighting module 300 in order to replace an auxiliary light module 400, an insert lighting module 300 may be removed in order to replace the entire insert lighting module 300, and in some cases to replace the insert lighting module 300 with a different number of auxiliary light modules 400 and/or different features. For example, an insert lighting module 300 with two auxiliary light modules 400 may be replaced with an insert lighting module 300 with only one auxiliary light module 400, for example as shown in FIGS. 7A and 7B. Additionally, an insert lighting module 300 with any number of auxiliary light modules 400 may be replaced with an insert lighting module 300 without any auxiliary light modules 400, for example an insert lighting module 300 as shown in FIGS. 10A and 10B. As shown in FIGS. 10A and 10B, an insert lighting module 300 may be substantially identical to the insert lighting module 300 of FIGS. 3A and 3B except that neither trim portion 309 includes an aperture 307 for an auxiliary light module 400 or a sensor 701. An insert lighting module 300 without auxiliary light modules 400 may be used when germicidal lights are no longer desired, and allow for easy replacement of the visible light engines 304 without completely removing the entire light fixture 100 from a ceiling. Instead of replacing an entire light fixture 100 when germicidal light is no longer desired, the reflector housing 200, including the visible light driver 902, may be left installed in a ceiling and only the insert lighting module 300 is replaced using the removal and insertion method discussed above. In some embodiments of light fixture 100, for example as shown in FIG. 10B, the visible light driver 902 of an insert lighting module 300 without auxiliary light modules 400 may be coupled to the insert housing 303.

The above-described aspects are merely possible examples of implementations, merely set forth for a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims that follow, they are used only in a generic and descriptive sense, and not for the purposes of limiting the described invention, nor the claims that follow.

The invention claimed is:

1. A light fixture comprising:
    a housing defining a channel; and
    an insert lighting module comprising:
        an insert housing;
        a visible light engine coupled to a bottom portion of the insert housing and configured to emit visible light for general illumination; and
        an auxiliary light module coupled to the insert housing and comprising an auxiliary light engine configured to emit germicidal light effective in deactivating pathogens,
    wherein a top portion of the insert lighting module, opposite the bottom portion, is positioned within the channel and the insert lighting module is coupled to the housing, and
    wherein the auxiliary light module is configured to be uncoupled and removed from the insert housing by performing the steps of:
        uncoupling the insert lighting module from the housing and removing the insert lighting module from the channel; and
        with the insert lighting module removed from the channel, uncoupling the auxiliary light module from the insert housing and removing the auxiliary light module from the top portion of the insert housing.

2. The light fixture of claim 1, wherein the auxiliary light engine is configured to emit ultraviolet germicidal light effective in deactivating pathogens.

3. The light fixture of claim 2, wherein the auxiliary light engine is configured to emit a dominant wavelength of 222 nm.

4. The light fixture of claim 3, wherein the auxiliary light engine comprises an excimer lamp.

5. The light fixture of claim 4, wherein the visible light engine comprises light emitting diodes.

6. The light fixture of claim 5, further comprising:
    a dosing circuit module electrically coupled to the auxiliary light engine and configured to provide power to and control the auxiliary light engine, wherein the dosing circuit module is not configured to provide power to nor control the visible light engine.

7. The light fixture of claim 6, further comprising:
    a visible light driver electrically coupled to the visible light engine and configured to provide power to and control the visible light engine,
    wherein the visible light driver is positioned within the housing and not coupled to the insert housing, and
    wherein the dosing circuit module is coupled to the top portion of the insert housing.

8. The light fixture of claim 6, wherein the dosing circuit module is configured to control the auxiliary light engine according to a repeating dosing scheme, and
    wherein the dosing scheme comprises a first period between 10 seconds and 2 minutes in duration wherein the auxiliary light engine emits the germicidal light followed by a second period between 1 minute and 10 minutes in duration wherein the auxiliary light engine does not emit the germicidal light.

9. The light fixture of claim 7, wherein the auxiliary light module further comprises a status indicator light,
    wherein the dosing circuit module is configured to determine an amount of remaining service life of the auxiliary light engine and control the status indicator light to provide different indications corresponding to the remaining service life of the auxiliary light engine, and wherein the different indication comprise a first indication corresponding to sufficient service life remaining, a second indication corresponding to a predetermine amount of service life remaining, and a third indication corresponding to the service life of the auxiliary light engine being reached.

10. The light fixture of claim 5, wherein a service life of the visible light engine is at least twice as long as a service life of the auxiliary light engine, and wherein the insert lighting module is configured so that the auxiliary light module can be replaced when the service life of the auxiliary light engine is reached with a substantially identical second auxiliary light module without replacing the visible light engine in order to operate the light fixture with both germicidal light and visible light beyond the service life of the auxiliary light engine.

11. The light fixture of claim 1, wherein the insert housing comprises a first trim portion, a second trim portion, and a central portion between the first trim portion and the second trim portion, wherein the visible light engine is coupled to the central portion, wherein the first trim portion defines a first aperture and a second aperture, wherein the auxiliary light module is positioned within the first aperture so that the germicidal light is emitted through the second aperture, wherein the insert housing further comprises an optic coupled to central portion and through which the visible light is emitted, and wherein the optic does not cover the second aperture so that the germicidal light does not pass through the optic.

12. The light fixture of claim 11, wherein the second aperture is smaller than the auxiliary light module so that the auxiliary light module cannot pass through the second aperture.

13. The light fixture of claim 11, wherein the first trim portion, the second trim portion, and the optic comprise curved profiles defining a flush curved bottom surface of the insert lighting module.

14. The light fixture of claim 11, further comprising a second auxiliary light module identical to the auxiliary light module, wherein the second trim portion defines a third aperture and a fourth aperture, wherein the second auxiliary light module is positioned within the third aperture so that germicidal light from a second auxiliary light engine of the second auxiliary light module is emitted through the fourth aperture, and wherein the optic does not cover the fourth aperture so that the germicidal light from the second auxiliary light engine does not pass through the optic.

15. The light fixture of claim 14, further comprising a dosing circuit module coupled to the top portion of the insert housing, wherein the dosing circuit module is electrically coupled to the auxiliary light engine and the second auxiliary light engine and configured to provide power to and control the auxiliary light engine and the second auxiliary light engine.

16. The light fixture of claim 11, further comprising:
an occupancy sensor coupled to the second trim portion; and
a visible light driver electrically coupled to the visible light engine and the occupancy sensor, and wherein the visible light driver is configured to provide power to and control the visible light engine based on signals from the occupancy sensor.

17. A method of replacing the auxiliary light module of the light fixture of claim 1, the method comprising:
uncoupling the insert lighting module from the housing, with the housing installed in a ceiling, and removing the insert lighting module from the channel;
uncoupling the auxiliary light module from the insert housing, with the insert lighting module removed from the channel, and removing the auxiliary light module from the top portion of the insert housing;
with the auxiliary light module removed, inserting a second auxiliary light module, identical to the auxiliary light module and comprising a second auxiliary light engine, into the top portion of the insert housing and coupling the second auxiliary light module to the insert housing; and
positioning the insert housing coupled to the second auxiliary light module within the channel of the housing installed in the ceiling, and coupling the insert lighting module to the housing.

18. The method of claim 17, further comprising:
uncoupling a first dosing circuit module coupled to the top portion of the insert housing, with the insert lighting module removed from the channel, wherein the first dosing circuit module is electrically coupled to the auxiliary light engine and configured to provide power to and control the auxiliary light engine;
coupling a second dosing circuit module to the top portion of the insert housing, after uncoupling the first dosing circuit module is removed from the channel; and
electrically coupling the second dosing circuit module to the second auxiliary light engine in order to provide power to and control the second auxiliary light engine.

19. A method of replacing the insert lighting module of the light fixture of claim 1, the method comprising:
uncoupling the insert lighting module from the housing, with the housing installed in a ceiling, and removing the insert lighting module from the channel;
with the insert lighting module removed from the channel, positioning a second insert housing of a second insert lighting module within the channel of the housing installed in the ceiling, and coupling the second insert lighting module to the housing, wherein the second insert lighting module comprises a second visible light engine coupled to a second bottom portion of the second insert housing and configured to emit visible light for general illumination.

20. The method of claim 19, wherein the second insert light module does not include any auxiliary light engines configured to emit germicidal light effective in deactivating pathogens.

\* \* \* \* \*